United States Patent [19]

Wingard

[11] 4,150,038
[45] Apr. 17, 1979

[54] CONVERSION OF HESPERIDIN INTO HESPERETIN

[75] Inventor: Robert E. Wingard, Palo Alto, Calif.

[73] Assignee: Dynapol, Palo Alto, Calif.

[21] Appl. No.: 797,105

[22] Filed: May 16, 1977

[51] Int. Cl.² .......................................... C07D 311/32
[52] U.S. Cl. .................................................. 260/345.2
[58] Field of Search ..................................... 260/345.2

[56] References Cited

PUBLICATIONS

Pritchett et al., J. Amer. Chem. Soc., 68, 2108 (1946).
Looker et al., J. Org. Chem., 25, 1829 (1960).

Primary Examiner—Nicky Chan
Attorney, Agent, or Firm—William H. Benz

[57] ABSTRACT

An improved procedure for the conversion of commercial hesperidin into high-purity, crystalline hesperetin is disclosed. This procedure comprises purifying the crude starting material by insolubles removal and precipitation, followed by cleaving the saccharides with a strong mineral acid in lower primary alkanol. The use of lower alkanol in this transformation facilitates the isolation of a high purity product uncontaminated by resinified sugars.

6 Claims, No Drawings

CONVERSION OF HESPERIDIN INTO HESPERETIN

BACKGROUND OF THE INVENTION AND REVIEW OF THE PRIOR ART

Horowitz et al. reported in U.S. Pat. No. 3,087,821 that citrus peels contained glycosidic flavanoids which could, by way of simple chemical modification, be converted into a new class of sweet compound. They discovered, for example, that neohesperidin, a bitter flavanone 7-$\beta$-neohesperidoside found in the Seville orange, provided an intensely sweet dihydrochalcone (1000X sucrose, molar basis) upon alkaline hydrogenation. Recently published findings demonstrate that nonglycosidic dihydrochalcones are also intensely sweet. Hesperetin dihydrochalcone derivatives bearing simple 4-O-carboxyalkyl (Crosby et al., U.S. Pat. No. 3,976,790) and 4-O-sulfoalkyl (Crosby et al., U.S. Pat. No. 3,974,299) substituents have been found to have excellent water solubility and to display taste properties that compare favorably with neohesperidin dihydrochalcone. The simplicity of these analogs suggests the possibility of economic preparation and renders them attractive candidates for potential development as food additives.

A straightforward and generally applicable means for preparation of these simplified sweeteners is shown in U.S. Pat. Nos. 3,976,790 and 3,974,299. The method involves the regioselective alkylation and direct alkaline hydrogenation of the flavanone hesperetin (1).

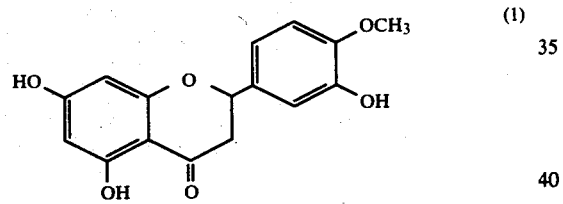

(1)

This aglycone, being the basic building block for these sweeteners, must be readily obtainable in quantity and in a high state of purity. Although hesperetin can be prepared by total synthesis (Zemplen and Bognar, Chem. Ber. 75B, 1043, 1942 or Honohan et al., J. Agric. Food Chem. 24, 906, 1976), a more economical preparation is the acidic hydrolysis of the naturally occurring rutinoside hesperidin (2), which is the main flavanoid constituent of lemons and oranges.

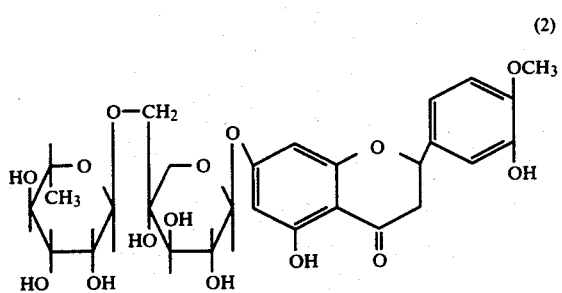

(2)

Hesperidin is produced commercially or may be extracted from chopped and pulped orange peels with alkali and isolated by filtration following neutralization, as taught by R. H. Higby in U.S. Pat. No. 2,421,061 (1947). Material prepared in this manner, or as obtained commercially, is not directly suitable for conversion into high quality hesperetin.

Analysis of commercial hesperidin (Sunkist Growers, Inc., Ontario, California), by high pressure liquid chromatography (HPLC), shows the presence of six uv-active impurities. These minor impurities, which are very similar in polarity to hesperidin, are composed of other phenolic glycosides also present in the citrus peel. Additionally, commercial hesperidin contains a significant amount of dark, insoluble residue which is presumably cellulose-like in nature. The estimated purity of this material is 70–75%. These impurities interfere with the preparation of high purity crystalline hesperetin.

Pritchett et al. in J. Am. Chem. Soc. 68, 2108 (1946) shows a process for the purification for hesperidin involving treating a formamide solution of hesperidin with activated charcoal followed by filtration and two serial ambient temperature nonstirred recrystallizations. Although this procedure does give an acceptable purity product, it does involve two multi-hour recrystallizations and achieves commercially unattractive low yields of the purified intermediates.

The acid catalyzed degradation of hesperidin (2) into hesperetin (1), rhamanose, and glucose (Equation A) was first carried out by Tiemann et al., Chem. Ber. 14, 946 (1881).

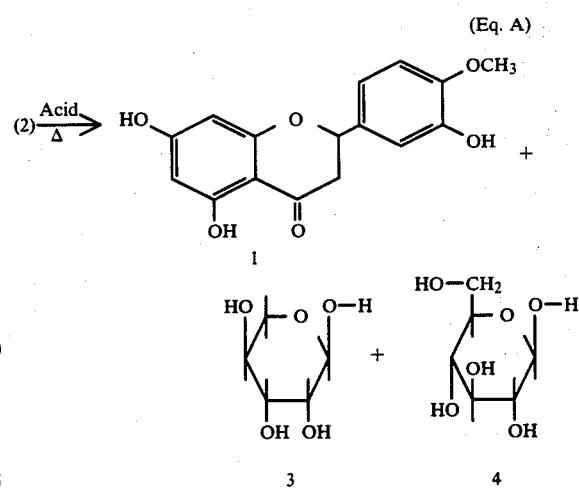

(Eq. A)

This old method, which employs aqueous sulfuric acid at elevated temperatures in the presence of an alcoholic cosolvent, has been used with little modification by most modern workers such as Looker at al., J. Org. Chem. 25, 1829 (1960). It suffers in that hesperidin is essentially insoluble in aqueous media and, therefore, extended reaction times (or pressure vessels) are required. Furthermore, the high temperatures and long reaction times cause the sugars to decompose into water-insoluble resinous materials. This leads to the isolation of a discolored and impure product. Recrystallization of the crude hesperetin obtained by this method will not effectively remove these resinous impurities. Adsorbents, such as activated carbon or acidic alumina, will remove these materials, but not without drastically lowering the yield.

Another low yield process for obtaining high purity hesperetin is shown by Arakawa et al. in Justus Liebigs Ann. Chem. 636, 111 (1960). Arakawa et al. first carry out a fractional crystallization of hesperidin from methanol. Then they hydrolyze the hesperidin very dilute (0.5%) in methanolic sulfuric acid followed by a fractional crystallization of the resulting hesperetin from methanol/water. This process yields but 4.3 g of final product from 50 g of starting material — a yield (8.6%) which is too low to be of interest commercially.

The present process is an improvement over these prior processes in that it gives high quality crystalline hesperetin in commercially viable yields.

STATEMENT OF THE INVENTION

The present invention provides an improved method for the conversion of crude commercial hesperidin to high purity crystalline hesperetin. This procedure comprises purifying the crude commercial hesperidin by insolubles removal and precipitation and then cleaving a high concentration of the hesperidin to hesperetin with a solution of a nonoxidizing strong mineral acid in lower primary alkanol and finally recovering the resulting hesperetin by precipitation in water. In a preferred aspect the present invention provides a process for preparing in high yield crystalline hesperetin of purity of not less than 97% by weight from crude hesperidin containing at least 5% of nonhesperidin impurities which comprises the steps of:

(a) Preparing a feed solution consisting essentially of 5 to 20% by weight of crude hesperidin in a polar aprotic solvent, (b) Treating said feed solution to remove insoluble impurities thereby forming a treated feed solution, (c) Adding said treated feed solution to at least about one-fourth its volume of stirred water at a temperature of at least 50° C., thereby forming a purified hesperidin solid precipitate and a liquid phase, (d) Isolating and recovering said purified hesperidin solid precipitate, (e) Admixing the purified hesperidin solid precipitate at a concentration of at least about 3% by weight with a substantial molar excess of nonoxidizing strong mineral acid in lower primary alkanol and maintaining the resulting admixture at an elevated temperature for a time sufficient to effect hydrolysis of the hesperidin into hesperetin, (f) Admixing said hesperetin with water, thereby forming a precipitate of crystalline high purity hesperetin, and (g) Thereafter recovering said precipitate of crystalline high purity hesperetin.

DETAILED DESCRIPTION OF THE INVENTION

The starting material for this process is commercial hesperidin. This material is available from Sunkist Growers, Inc., Ontario, California. In the quality known as "purified grade" it is composed of 30 to 15% or more of nonhesperidin impurities which are more fully described here in the Background. Other similar hesperidins, whether purchased or prepared, may be used as starting material as well.

In the first phase of the present process, the crude hesperidin is freed of insoluble impurities. This generally involves dissolving the hesperidin in a suitable solvent and separating out insolubles. Suitable solvents may be selected from the class of polar aprotic organic liquids such as members of the group of hexamethylphosphotamid, N-methylpyrolidone, tetramethylenesulfone (also known as Sulfolane ®) and the liquid amide solvents including dimethylformamide, formamide and N,N-dimethylacetamide. The liquid amide solvents make up a preferred group of solvents for this step with dimethylformamide (DMF) being a most preferred solvent.

The amount of solvent may advantageously be controlled so as to yield a concentration of crude hesperidin of from about 5% by weight to about 30% with concentrations of from 7% to 25% being preferred.

The separation of solution from insolubles may be effected by solid-liquid separation methods known in the art such as filtration or centrifugation. The step is complicated somewhat by the very fine size of the insolubles. Filtration through fritted glass or metal or a similar filter material of a porosity small enough to effectively remove its solids can often lead to filter plugging or very slow rates of filtration. It is generally preferred to use a filter aid or flocculating agent to increase the efficiency of filtration or centrifugation. Excellent results are achieved when diatomaceous earth such as the material marketed under the trademark Celite ® is employed as a filter aid. A bed of diatomaceous earth may be used as a filter as well. The amount of filter aid may be 0%, in view of its optional nature, or may range up to about 100% by weight based on the weight of hesperidin treated. Larger amounts could be used, but are not seen to offer any advantages and do represent potential expensive waste.

Following insolubles removal, the hesperidin is precipitated. This may be carried out by admixing the organic solvented solution of hesperidin with water. This admixing is preferably carried out with vigorous agitation and elevated temperatures. It is preferred to add the organic solution to stirred, heated water. For best results, the water temperature should be at least about 60° C. with temperatures of from 65 to 105° C. being preferred, temperatures of from 85 to 105° C. being more preferred, and reflux temperature being most preferred. The volume of water should be at least ¼ the volume of organic solvent, with water to solvent proportions of 1:3 to 2:1 being preferred. It is also of advantage (but not required) to acidify the water to pH 6 or less to minimize oxidative degradation. This may be accomplished by adding a small amount of a mineral such as HCl or $H_2SO_4$ or an organic acid such as acetic acid to the water. Preferably, the water is acidified to a pH of from 3.5 to 6, more preferably to a pH of from 3 to 6.

Following the precipitation, the solid purified hesperidin is recovered from the liquid phase. This may be effected by filtrating, settling and decanting, centrifuging or equivalent processes known to the art. The hesperidin recovery is generally carried out at a lower temperature than the precipitation. Typical useful temperatures are from ambient (15° C.) to about 50° C.

The precipitated and collected solid hesperidin may optionally be rinsed and/or dried before being converted to hesperetin. This conversion is as shown above in Equation A. It is the acid catalyzed hydrolysis cleavage of the saccharide groups off of the hesperidin.

The following parameters must be controlled during this reaction:

1. The reaction medium must be essentially neat lower primary alkanol.

2. The starting concentration of hesperidin in the alkanol must be at least 3% by weight.

3. The reaction must be effected at an elevated temperature.

4. The reaction must be carried out in the presence of a nonoxidizing strong mineral acid.

The reaction medium is lower primary alkanol, that is, 1 to 4 carbon atoms primary alkanol. Such materials include methanol, ethanol, n-propanol and n-butanol. Preferred alkanols are methanol and ethanol with methanol being most preferred. Mixtures of these alkanols may be used. Secondary and tertiary alkanols are generally considered not suitable as they dehydrate to water and olefin in the presence of strong mineral acid. The alkanols should be used essentially neat. This means that they may contain up to about 10% by weight water. Water contents of 0% to 5% are preferred.

The starting concentration of hesperidin should be in the range of from 3% to 30% by weight (basis alkanol plus acid) with concentrations of from 5% to 25% being preferred and concentrations of from 5% to 20% being more preferred. Lower concentrations are to be avoided as they lead to unacceptably low product yields.

The reaction temperature is elevated. When methanol is used as reaction medium, its atmospheric reflux temperature (65° C.) is very easy to achieve and control and is preferred. In general, any temperature from about 50° C. to about 90° C. can be employed. Higher temperature appears to increase the production of resinous impurities while lower temperatures give too slow a reaction time. Temperatures from 60° C. to 85° C. are preferred. The reaction time is, of course, inversely related to the temperatures employed. At 50° C. as much as 30 hours are required to complete the reaction. At 90° C. as little as three hours are needed. At 60-70° C. from 6 to 15 hours give full reaction.

As catalyst for this reaction is employed strong mineral acid. Such acids include sulfuric acid, and the halo acids, for example, hydrochloric, hydroiodic, hydrobromic, perchloric, periodic, hypochlorous and the like. Nitric acid is not employed as it is an oxidizing agent which will destroy hesperetin and lower the yield. Phosphorous-containing mineral acids, sulfurous acid and organic acids are too weak to effectively catalyze the desired reaction. The amount of mineral acid should be a catalytically effective amount. Such an amount is at least one equivalent of acid per mole of hesperidin with amounts of from about five equivalents to about 40 equivalents of acid per mole of hesperidin being preferred and amounts of from about 10 to about 30 equivalents of acid per mole of hesperidin being more preferred.

Following the acid-catalyzed cleavage reaction, the reaction mixture contains alkanol, acid, hesperetin and sugar residues. The hesperetin must be isolated from the reaction mixture. This may be effected very directly by adding the reaction mixture to heated water so as to cause the hesperetin to precipitate. Alternatively, the hesperetin may be extracted, made into a solution in a water-miscible organic and this organic solution added to water to cause the hesperetin to precipitate. On a laboratory scale the more complex latter route is acceptable. On a commercial scale, the direct precipitation route, being less complex, would probably be preferred.

With the direct precipitation method the acidic alkanol-solvented reaction product is added to heated agitated water. The amount of water is very suitably from about 0.5 to 10 times the volume of added reaction product — and preferably is from 1.0 to 6 times the volume of added reaction product. The water is heated suitably to at least about 50° C. and preferably from 50 to 110° C., more preferably from 65 to 105° C. The alkanol-solvented reaction product is added gradually such as over a period of 0.25 to 3 hours. With methanol- or ethanol-solvented reaction products, the alkanol at least partially goes overhead, which is of advantage. Following precipitation, the hesperetin is recovered as a solid such as by centrifugation, settling, filtration or equivalent process.

Optionally, a portion of the reaction product's alkanol may be removed such as by evaporation at atmospheric or subatmospheric pressure. The amount of alkanol removed should not be so great as to cause hesperetin to precipitate prior to adding the reaction product to the agitated water.

When the longer extraction process is employed, crude hesperetin is separated from the hydrolysis reaction product by extracting the hesperetin into a polar organic solvent, then recovering the hesperetin from the extract and dissolving it in a water-miscible organic liquid which solution is then subjected to the just described precipitation of the more direct route. The polar organic solvent should be relatively water insoluble. Nonsymmetric alkyl halides, such as methylene chloride, chloroform, and dichloroethane, and polar liquid alkyl esters such as ethyl acetate and methyl acetate, may be used as the polar organic solvent. Ethyl acetate and chloroform are preferred polar organic solvents. Mixtures of polar organics may be used as well.

The crude hesperetin containing extract is isolated and the solvent is removed by evaporation. The solid crude hesperetin is then taken up into a water-miscible organic. Examples of useful water-miscible organics are 1 to 4 carbon alkanols and alkandiols such as ethanol, methanol, isopropanol, ethylene glycol and propylene glycol, and 3 to 5 carbon alkanones such as dimethyl ketone, methyl-ethyl ketone and diethylketone, and tetrahydrofuran, dimethoxyethene and dioxane and mixtures thereof. Acetone and methanol are preferred water-miscible organics with acetone being the more preferred.

The amount of water-miscible organic should be as little as possible to dissolve the hesperetin. Generally, a solution containing from 5 to 25% w hesperetin can be prepared. The volume of water-miscible organic is from 0.05 to about 1 times the volume of precipitation water.

With this process, it is desirable to acidify the precipitation water, preferably to a pH of 3 to 6 with an acid such as acetic acid or sulfuric acid. This acidification is not needed, since acid is already present, if the extraction is omitted. In this process it may be of advantage to blanket one or more steps with an inert atmosphere such as nitrogen or argon.

The overall yields of hesperetin achieved by this process are high. Based on the maximum amount of hesperetin theoretically possible in the feed, yields of at least 70% and more, usually 75 to 90% are attained.

The present invention will be further illustrated by the following Examples. These are intended to exemplify the invention and are not to be construed as limiting its scope.

EXAMPLE I

A. A 2-l., three-neck flask, equipped with overhead stirrer and argon inlet, was charged with 100 g of hesperidin (Sunkist Growers, Inc., Ontario, California, Lot No. 6165 - W-3), about 75% purity and 1-l. of dimethylformamide (DMF). The dark mixture was stirred rapidly for 30 min, treated with diatomaceous earth — Celite ® (50 g), and filtered through a 50 g pad of the same material with 200 ml of DMF being used for washing. The clear yellow DMF solution was added dropwise over 90 min to a continuously boiling mixture of 1 l. of $H_2O$ and 25 ml of acetic acid contained in a 3-l., three-necked flask equipped with overhead stirrer, reflux condenser, heating mantle, and dropping funnel topped with an Ar inlet. Purified hesperidin began to crystallize from the medium after 300 ml of solution had been added.

B. The slurry was cooled to 40° C. with continued stirring, filtered, and the residue washed with warm $H_2O$ (1 × 1 l.), isopropanol (1 × 0.5 l.), and dried in vacuo (50° C.) to afford 62.6 g of fluffy white hesperidin.

C. A 2-l., three-neck flask, equipped with magnetic stir bar and condenser, was charged with 50.0 g (81.8 mmol) of purified hesperidin, 1 l. of dry $CH_3OH$, and 50 ml of 96% $H_2SO_4$. The solution was refluxed for 7.5 hr.

D. The reaction mixture was poured into 4 l. of ethyl acetate. The mixture was washed with 15% aqueous NaCl (1 × 1 l.), $H_2O$ (3 × 1.5 l., final wash colorless), brine, and dried ($Na_2SO_4$). Evaporation afforded 27.1 g of pale yellow powder.

E. The crude product was dissolved in acetone (200 ml) and added dropwise (60 min) to a vigorously stirred (overhead) mixture of 3 l. of $H_2O$ and 20 ml of acetic acid maintained at 95–100° C. The slurry was cooled to 45° C. and the hesperetin filtered and dried in vacuo (24.4 g, 85% yield based on fed hesperidin). The product's identity was confirmed and its purity shown to be 97+%.

EXAMPLES II-VI

The preparation of Example I is repeated 5 times with modifications achieving essentially the same results.

In Example II formamide is substituted for DMF in Step A.

In Example III centrifugation is substituted for filtration in Step H.

In Example IV 25 ml of $H_2SO_4$ is employed in Step C.

In Example V 0.90 mol of HCl is substituted for $H_2SO_4$ in Step C.

In Example VI chloroform is substituted for ethyl acetate in Step D.

EXAMPLE VII

A. A 500-liter glass-lined reactor equipped with an overhead stirrer is charged with 25 kg of commercial hesperidin (75% purity) and 250 liters of DMF and stirred under nitrogen until the hesperidin dissolves. Diatomaceous earth filter aid (10 kg) is added and mixed for 10 minutes. The product is then fed to a continuous centrifugal separator where solid residues and diatomaceous earth are spun down and a solid-free DMF solution of hesperidin is formed. The DMF solution is then added over 45 minutes to 300 liters of stirred refluxing pH 4 water in a 500 liter reactor. The reflux is contained for 20 minutes, the mixture is cooled to ambient and filtered to yield crystalline hesperidin which is rinsed with water and dried.

B. Hesperidin (10 kg) is charged to the 500 liter stirred reactor under nitrogen along with 150 liters of absolute methanol and 10 kg of concentrated $H_2SO_4$. The mixture is stirred at reflux for 5 hours. Then, 50 liters of methanol are taken off overhead over 3 hours. The 100 liters of product is then gradually fed over 2 hours to 400 liters of vigorously stirred boiling 95–100° C. water under nitrogen. The hesperetin precipitates. The water is cooled and the solid hesperetin is recovered in 85+% yield from the water by filtration. After water rinsing thrice, the hesperetin is dried. Analysis indicates that it is 97%+ pure.

What is claimed is:

1. The process of preparing in high yield crystalline hesperetin of purity of not less than 97% by weight from crude hesperidin containing at least 5% of nonhesperidin impurities which comprises the steps of:
   a. Preparing a feed solution consisting essentially of 5 to 30% by weight of crude hesperidin in a polar aprotic liquid amide solvent,
   b. Treating said feed solution to remove insoluble impurities thereby forming a treated feed solution,
   c. Adding said treated feed solution to at least about one-fourth its volume of stirred water at a temperature of at least 50° C. thereby forming a purified hesperidin solid precipitate and a liquid phase,
   d. Isolating and recovering said purified hesperidin solid precipitate,
   e. Admixing the purified hesperidin solid precipitate at a concentration of at least about 3% by weight with a substantial molar excess of sulfuric acid in methanol and maintaining the resulting admixture at an elevated temperature for a time sufficient to effect hydrolysis of the hesperidin into hesperetin,
   f. Admixing said hesperetin with water thereby forming a precipitate of crystalline high purity hesperetin, and
   g. Thereafter recovering said precipitate of crystalline high purity hesperetin.

2. The process of preparing in high yield crystalline hesperetin of purity of not less than 97% by weight from crude hesperidin containing at least 5% of nonhesperidin impurities which comprises the steps of:
   a. Preparing a feed solution consisting essentially of 5 to 30% by weight of crude hesperidin in a polar aprotic liquid amide solvent,
   b. Treating said feed solution by filtering in the presence of diatomaceous earth to remove insoluble impurities thereby forming a treated feed solution,
   c. Adding said treated feed solution to at least about one-fourth its volume of stirred water at a temperature of at least 50° C. thereby forming a purified hesperidin solid precipitate and a liquid phase,
   d. Isolating and recovering said purified hesperidin solid precipitate,
   e. Admixing the purified hesperidin solid precipitate at a concentration of at least about 3% by weight with a substantial molar excess of sulfuric acid in a solvent consisting essentially of, methanol and maintaining the resulting admixture at an elevated temperature of from about 50° C. to about 90° C. for a time of from 3 hours to 30 hours sufficient to effect hydrolysis of the hesperidin into hesperetin,
   f. Admixing said hesperetin with water thereby forming a precipitate of crystalline high purity hesperetin, and
   g. Thereafter recovering said precipitate of cyrstalline high purity hesperetin.

3. The process of claim 2 wherein in Step (f) said admixing is carried out at a temperature of from 50° C. to 110° C.

4. The process of claim 3 wherein to intermediate Steps (e) and (f) is added an additional Step (e') comprising (e') separating crude hesperetin from the hydrolysis product by extracting the hesperetin into a polar organic solvent, then recovering the hesperetin and dissolving it in a watermiscible organic liquid.

5. The process of claim 4 wherein said polar organic solvent is ethylacetate.

6. The process of claim 5 wherein in each of Steps (c) and (f) said water is acidified to a pH of 6 or less.

* * * * *